United States Patent [19]

Hofmann

[11] Patent Number: Plant 5,314

[45] Date of Patent: Oct. 30, 1984

[54] VARIETY OF GERANIUM NAMED 'JUBILAEUM'

[75] Inventor: Guenter Hofmann, Dresden, German Democratic Rep.

[73] Assignee: Oglevee Associates, Inc., Connellsville, Pa.

[21] Appl. No.: 478,144

[22] Filed: Mar. 23, 1983

[51] Int. Cl.[3] ..... A01H 5/00

[52] U.S. Cl. ..... Plt./68

[58] Field of Search ..... Plt./68

*Primary Examiner*—James R. Feyrer

*Attorney, Agent, or Firm*—Webb, Burden, Robinson & Webb

[57] ABSTRACT

A new geranium cultivar is distinguished by its brilliant color, short and compact plant, more basil branching, close internodes, small leaves and short flower stems with the flowers positioned immediately atop the foliage. The new cultivar is further distinguished by its uniformity and symmetry as compared with commonly grown zonal geraniums.

3 Drawing Figures

BACKGROUND OF THE NEW PLANT

The present invention comprises a new and distinct cultivar of *Pelargonium hortorum,* Bailey known by the varietal name of Jubilaeum. The new variety was discovered in a selective breeding program and is a seedling resulting from the cross of the seed parent Rubin and the pollen parent Bruni.

The new cultivar was discovered in the year 1980 in Dresden, German Democratic Republic; was first asexually reproduced by cuttings in Dresden, German Democratic Republic and has been repeatedly asexually reproduced by cutting at Oglevee Floral Company in Connellsville, Pa. over an eighteen month period. It has also been trialed and field tested at Connellsville during the summers of 1981 and 1982. It has been found to retain its distinctive characteristics through successive propagations.

The new cultivar, when grown in a greenhouse in Connellsville, Pa., using natural light and 62° F. night temperature and 70° F. day temperature, has a response time of five weeks from a well rooted cutting to a flowering plant in a four inch (10 cms.) pot.

DESCRIPTION OF THE DRAWING

FIG. 1 is a graph of the flavonols fingerprinting;

DESCRIPTION OF THE NEW PLANT

Figure 1:
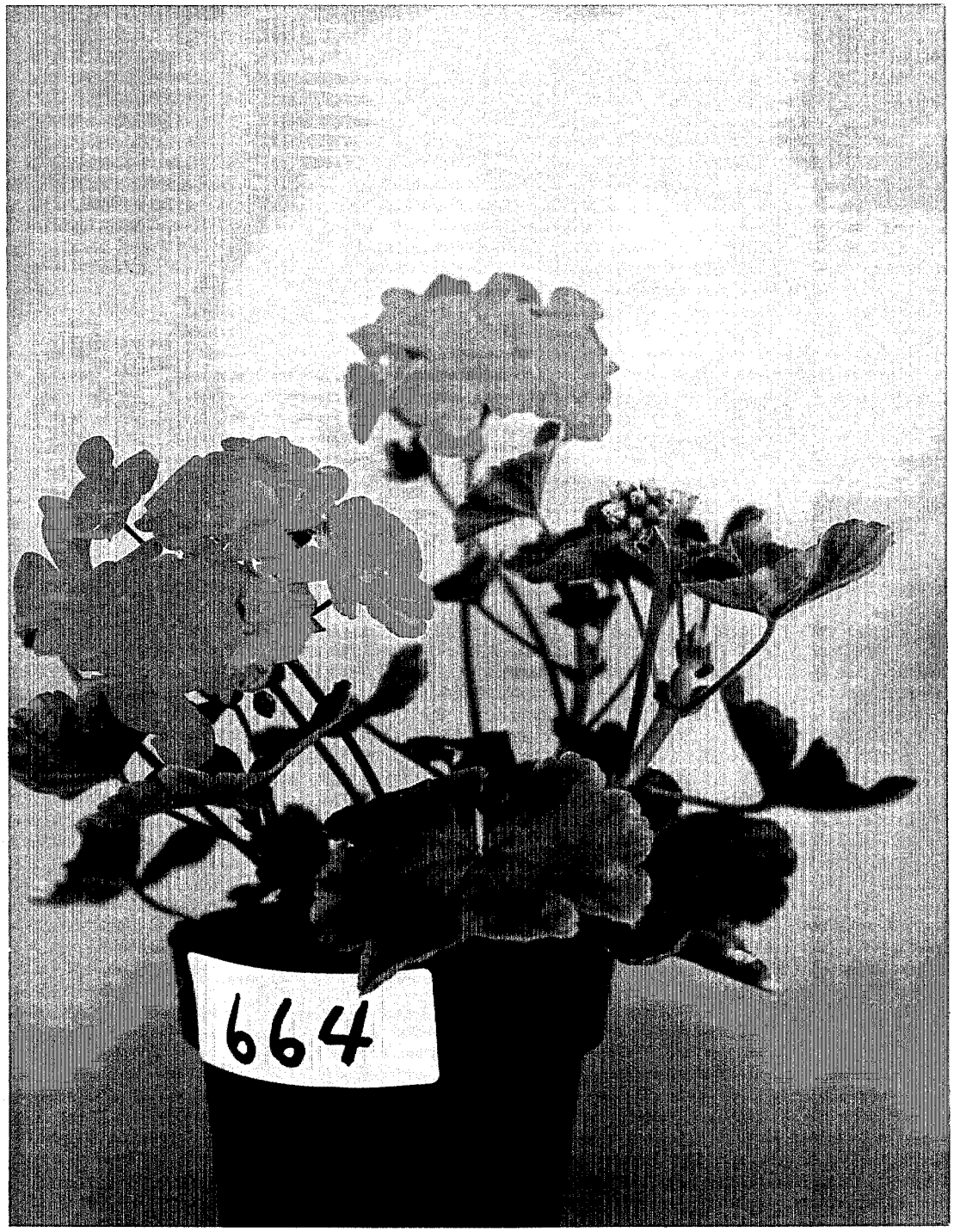
FIG. 1 of the accompanying photographic drawing illustrates the new cultivar, the color being as nearly true as possible with color illustrations of this type.

The following detailed descriptions set forth the characteristics of the new cultivar. The data which define these characteristics were collected from asexual reproductions carried out by the Oglevee Floral Company in Connellsville, Pa. The plant history was taken on five week plants, blossomed under natural light in a greenhouse and color readings were taken indoors under 100 foot candles of cool, white fluorescent light. Color references are primarily to the R.H.S. Colour Chart of The Royal Horticultural Society of London.

THE PLANT

Classification:

*Botanical.*—*Pelargonium hortorum,* Bailey.

*Commercial.*—Zonal geranium.

Form: Bush.

Height: 12 To 18 cms. (15 cms. average) as a four inch pot plant excluding bloom and 22 to 24 cms. (23 cms. average) as a four inch pot plant including bloom.

Growth: Short and compact with more basil branching, closer internodes and smaller leaves as compared with commonly grown zonal geraniums.

Strength: Very sturdy with a low susceptibility to wind and rain damage.

Foliage: The quantity of foliage is of below average abundance.

Leaves:

*Size.*—7 To 9 cms. across.

*Shape.*—Reniform with oblique base and pronounced upward cupping.

*Margin.*—Cuneate.

*Texture.*—Leathery and pubescent.

*Color.*—Upperside — Fan 3 Green Group 137A. Underside — Fan 3 Green Group 138B.

*Ribs and veins.*—Palmate.

Petioles: 5 To 7cms.

Stem:

*Color.*—Fan 3 Yellow Green Group 143A

*Internodes.*—1 To 2 cms.

THE BUD

Shape: Umbel formed with approximately 40 florets.

Size: As bud develops at first color show, head size is 3 cms. and it opens into a fully developed head size of 9 to 10 cms. in diameter.

INFLORECENCE

Blooming habit: Continuous throughout the year.

Size: 9 To 10 cms. across.

Borne: Singly in an umbel form.

Florets:

*Form.*—Some reflexing and some flat to slightly cupped; non-symmetrical and irregular in shape.

*Petals.*—8 To 10 in number, plus 2 to 3 petaloids.

*Upperside.*—Predominant area Fan 1 Red Group 40A, some outer area Fan 1 Red Group 44B, plus pencil thin veining at base of petal similar in color to outer area of petal. Note: The color of the petal upperside is difficult to identify because of rough textured surface; angle of observation causes color change due to different appearance of refracted light.

*Underside.*—Fan 1 Orange Red Group 33A for the central position and Fan 1 Orange Red Group 34A along outer portion.

*Size.*—5 cms.

*Texture and appearance.*—Firm and satiny.

Petaloids:

*Quantity.*—2 To 3 in number.

*Shape.*—Small and twisted.

*Color.*—Same as Florets.

Pedicel:

*Length.*—2.5 To 3 cms.

Peduncle:

*Length.*—12 To 14 cms.

Persistance: Slight shattering.

Disease resistance: Acceptable to Botrytis.

Lasting quality: On the order of three weeks.

REPRODUCTIVE ORGANS

Stamens:

*Anthers.*—2 To 10, imperfectly formed.

*Filaments.*—10 In number, flattened, white at base and red at tips. 0.5 to 1 cm. in length.

*Pollen.*—Brownish Yellow

Pistils:

*Number.*—1.

*Length.*—1 cm.

*Stigma.*—5 Arms upright, reddish purple in color.

*Style.*—0.5 cm. and reddish purple in color.

Ovaries: Green, 5 carpels.

Fruit: Nonfertile.

The following evaluation is a result of the trialing and field testing carried out in the summer of 1982 at Connellsville, Pa., and compares the new geranium cultivar to the standard cultivar "Hildegaard" presently commercialized in the United State. The ratings are taken on plants planted in June and evaluated as to height, flowering, number of flowers, heat tolerance and form. The rating is based on a weighted average. A rating of 1.0 is poor and a rating of 10.0 is outstanding.

| CULTIVARS | EVALUATIONS 7/13/82 | 8/15/82 | 9/15/82 | AVERAGE SEASONAL RATING |
|---|---|---|---|---|
| JUBILAEUM | 8.0 | 7.5 | 8.0 | 7.8 |
| HILDEGAARD | 5.0 | 5.0 | 5.0 | 5.0 |

The new cultivar is characterized by its brilliant color and its short and compact plant. There is more basil branching and close internodes and small leaves as compared with the standard bush zonal geraniums produced in the United States. A short flower stem positions the flower immediately atop of the foliage into the plant and renders the plant very resistant to wind and rain damage. The new cultivar is further characterized by its early flowering and its floriferousness. The new cultivar is similar to Alex (patent pending) except that it has more flowers than Alex and is more uniform and symmetrical in shape than Alex.

Figure 2:
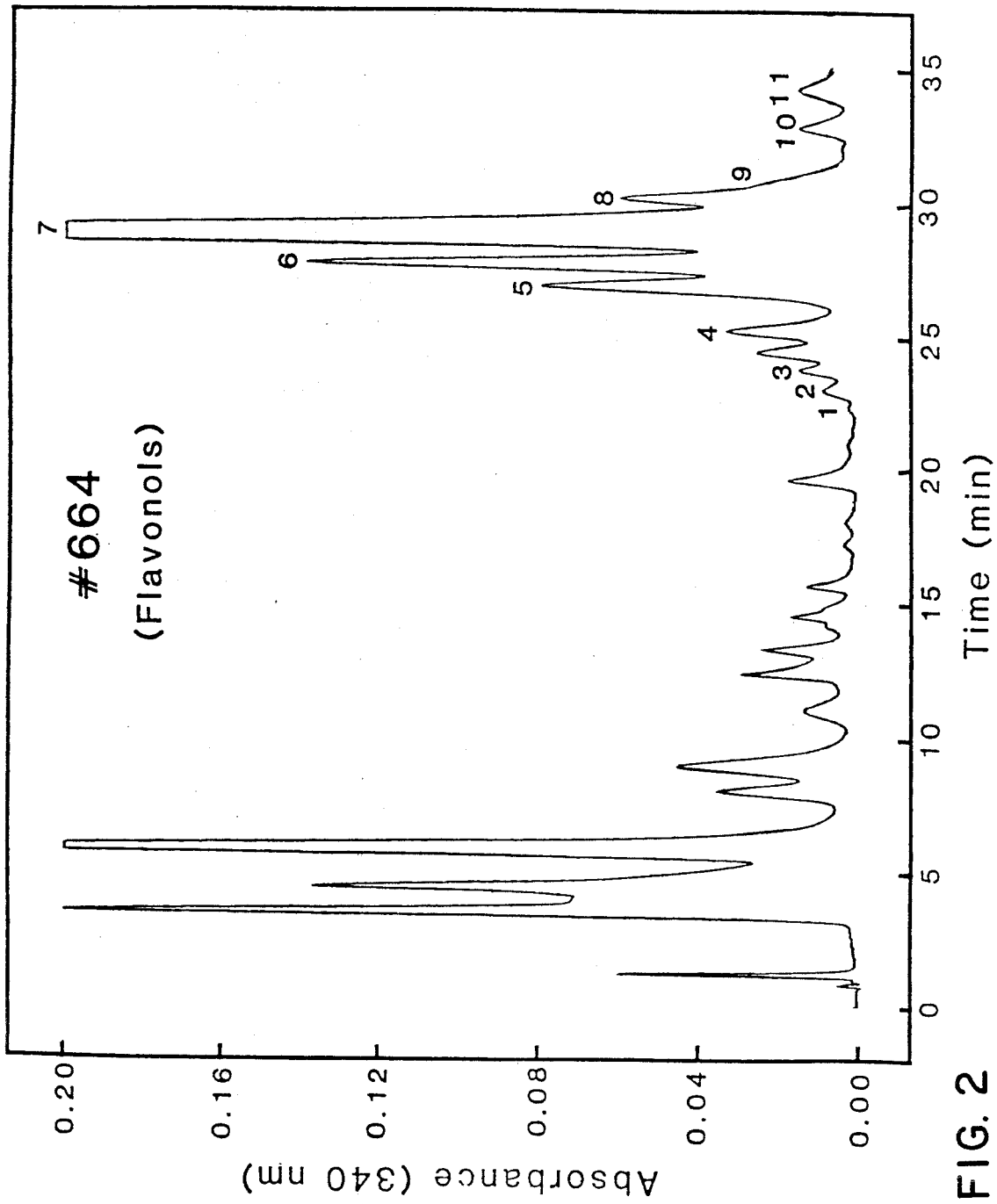
FIG. 2 is a graph of flavonols fingerprinting.
Figure 3:
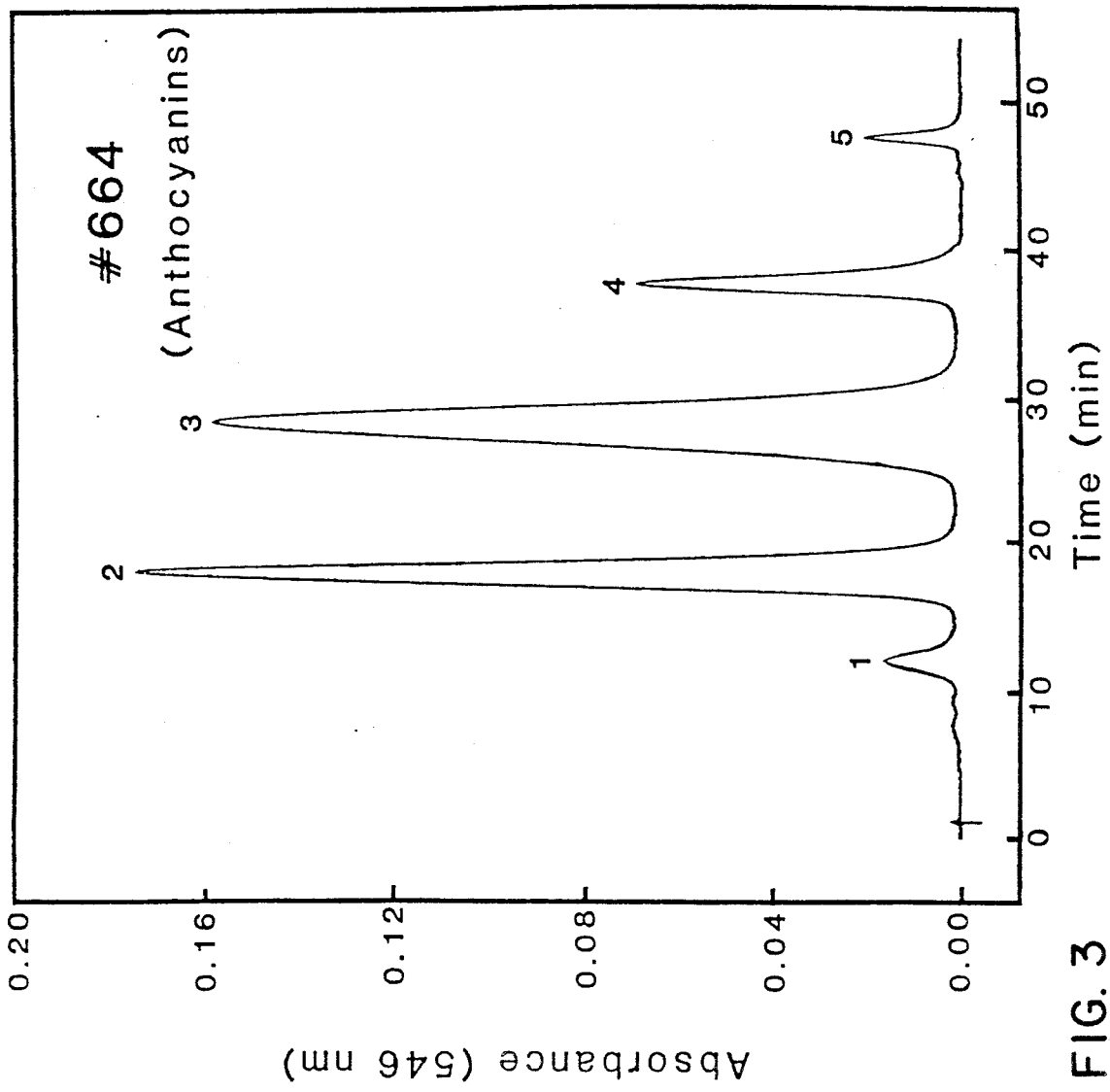
FIG. 3 is a graph of the anthocyanins fingerprinting of the new cultivar.

The new cultivar has been fingerprinted by the United States Department of Agriculture, Florist and Nursery Crops Laboratory, Beltsville, Md. Young plants arrived from Oglevee Floral Company of Connellsville, Pa. and were grown under standard conditions in a greenhouse at Beltsville, Md. The fingerprinting was conducted by high pressure liquid chromatographic analysis of the anthocyanin and flavonol chemical markers utilizing flower petals as an adjunct for cultivar identification. Petals were selected for analysis from individual mature flowers sampled just after anthesis. It should be noted that changes in environment can influence the biosynthesis of the flavonoids. The absorption profiles (fingerprints) are illustrated in FIGS. 2 and 3.

I claim:

1. A new and distinct variety of geranium plant substantially as shown and described.

* * * * *

UNITED STATES PATENT AND TRADEMARK OFFICE

CERTIFICATE OF CORRECTION

Plant
PATENT NO. : 5,314

DATED : October 30, 1984

INVENTOR(~~S~~) : Guenter Hofmann

It is certified that error appears in the above-identified patent and that said Letters Patent are hereby corrected as shown below:

Column 1 Line 13 "cutting" should read --cuttings--.

Column 1 Line 30

Delete --FIG. 1 is a graph of the flavonols fingerprinting;--.

Claim 1 - Column 4 Line 42 Before "shown" insert --herein--.

Signed and Sealed this

*Ninth* Day of *April 1985*

[SEAL]

*Attest:*

DONALD J. QUIGG

*Attesting Officer* *Acting Commissioner of Patents and Trademarks*